(12) United States Patent
Lott (10) Patent No.: US 7,285,262 B2
(45) Date of Patent: *Oct. 23, 2007

(54) NATURAL SUNLIGHT PHOTOSTABLE COMPOSITION

(75) Inventor: Dennis Lee Lott, Flagler Beach, FL (US)

(73) Assignee: Tanning Research Laboratories, Inc., Armond Beach, FL (US)

( * ) Notice: Subject to any disclaimer, the term of this patent is extended or adjusted under 35 U.S.C. 154(b) by 19 days.

This patent is subject to a terminal disclaimer.

(21) Appl. No.: 10/887,464

(22) Filed: Jul. 8, 2004

(65) Prior Publication Data

US 2005/0025727 A1 Feb. 3, 2005

Related U.S. Application Data

(60) Provisional application No. 60/486,194, filed on Jul. 11, 2003.

(51) Int. Cl.
*A61Q 17/00* (2006.01)
*A61Q 17/04* (2006.01)
*A61Q 19/04* (2006.01)
*A61K 8/02* (2006.01)

(52) U.S. Cl. .......................... 424/59; 424/60; 424/400; 424/401

(58) Field of Classification Search .................. 424/59, 424/60, 400, 401
See application file for complete search history.

(56) References Cited

U.S. PATENT DOCUMENTS 6,436,376 B1 * 8/2002 Hansenne et al. ............ 424/59

* cited by examiner

*Primary Examiner*—Shelley A. Dodson
(74) *Attorney, Agent, or Firm*—Louis C. Paul (57) ABSTRACT

The present invention relates to photostable compositions that provide protection from ultraviolet radiation ("UVR"). The invention particularly relates to the sunscreens avobenzone, octocrylene and oxybenzone, forming a triplet sunscreen combination. Compositions of the present invention are generally substantially free of substantial amounts of other sunscreens. The triplet combination surprisingly provides and substantially maintains the initial SPF value of the sunscreen composition throughout the period of UVR exposure. Compositions of the invention are photostable such that each of sunscreen active in the triplet combination does not appreciably photodegrade. The present invention accurately communicates the amount of UVR photoprotection actually provided in natural sunlight and minimizes the amount of potential harmful free radicals formed as byproducts of photodegradation.

32 Claims, 1 Drawing Sheet

Figure 1

NATURAL SUNLIGHT PHOTOSTABLE COMPOSITION

CROSS-REFERENCE TO RELATED APPLICATIONS

This application claims priority to U.S. Provisional Application Ser. No. 60/486,194, filed Jul. 11, 2003.

STATEMENT REGARDING FEDERALLY-SPONSORED RESEARCH OR DEVELOPMENT

Not Applicable.

FIELD OF THE INVENTION

The field of invention of the present invention relates to photostable compositions that provide protection from ultraviolet radiation ("UVR"). The invention particularly relates to the sunscreens avobenzone, octocrylene and oxybenzone, forming a triplet sunscreen combination.

BACKGROUND OF INVENTION

It is well-documented that exposure to ultraviolet radiation ("UVR") can result in a wide range of adverse health consequences. Excessive exposure to UVB light (290-320 nm) can have both short and longer-term effects. The immediate and primary consequence of unprotected UVB exposure is erythema and sunburn Longer term, childhood sunburns have been correlated with melanoma later in life. UVA light (320-400 nm) penetrates deeper than UVB, reaching both the epidermis and dermis. Repeated exposure to the shorter wavelength UVA II rays (approximately less than about 340 nm) and the longer wavelength UVA I rays (approximately longer than about 340 nm) have been associated with formation of fine lines and wrinkles, irregular skin pigmentation, weakening of the skin's immune system and skin cancer. Other skin disorders associated with overexposure to UVR include non-melanoma skin cancers (i.e., basal cell carcinomas and squamous cell carcinomas), actinic keratoses and premature aging of the skin.

Sunscreen products absorb a certain percentage of light over a specified spectrum, thus preventing potentially harmful erythemal UVR from reaching and damaging the skin. The sun protection factor ("SPF") listed on sunscreen products is related to this percentage and is intended to communicate the amount of erythemal UVR attenuation. More particularly, numerical SPF theoretically tells the user that he or she is protected X times longer than without sunscreen where X is the labeled SPF. For example, an SPF 33 product would, theoretically, absorb 97% of erythemal UVR and allow 3% of unattenuated light to reach the skin. The user of such an SPF 33 product would conclude that he or she could stay out in the sun 33 times longer than without the sunscreen. However, because most sunscreens are not photostable, labeled SPF is not indicative of the photoprotection actually provided, and thus misleads consumers to believe that they can safely stay out in sun for longer periods of time than that for which the sunscreen actually provides protection. Accordingly, one objective of the present invention is to develop a photostable sunscreen whose labeling accurately communicates to consumers the degree of UVR protection actually provided. Another object of the invention is to provide a sunscreen composition that substantially maintains its SPF rating over an exposure time period of a typical consumer.

One shortcoming of currently available sunscreen products identified by the inventor is that SPF ratings are generated on the basis of sunscreen product exposure to artificial light spectra generated in a solar simulator. While convenient to the chemist testing a formulation, the SPF methodology does not satisfactorily provide an accurate measure of how the formulation will perform under actual conditions of use. Without being bound by theory, the deficiency is believed to be that wavelengths present in natural sunlight that are missing in the artificial spectra, or are present in much lesser relative amounts than in natural sunlight, are responsible (at least in part) for degradation reactions in many sunscreens. These degradation reactions result in lesser amounts of effective sunscreen being present over the exposure time so that effective SPF drops with exposure time. These degradation reactions also generate free radicals, which are associated with adverse health consequences.

Figure 1:
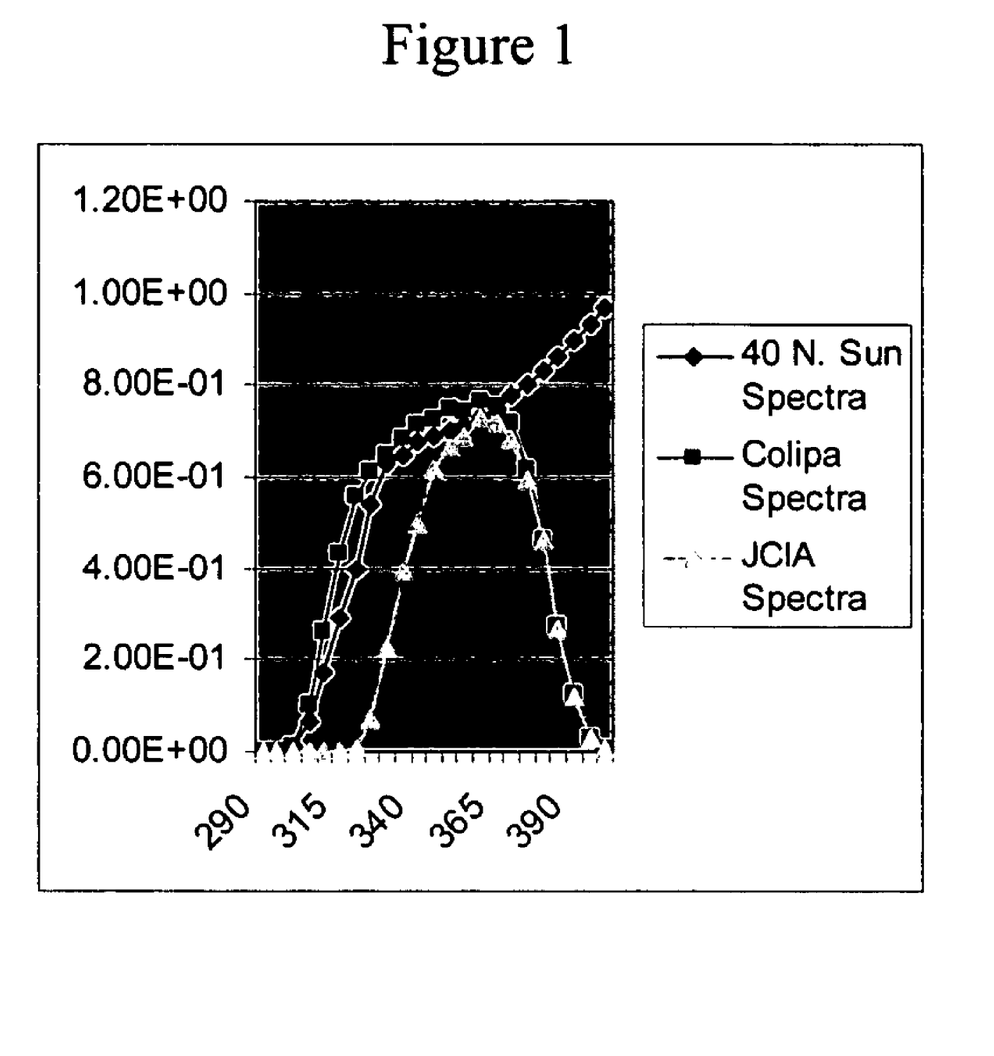
FIG. 1 shows COLIPA, JCIA and SSS spectra.

The most commonly used simulator is a Xenon Arc solar simulator equipped with a WG320 filter, a UG11 filter, and a dichroic mirror. Such a simulator can produce light spectra meeting the SPF testing specifications set by the European Cosmetic Toiletry and Perfumery Association ("COLIPA") and routinely used in the US as a spectra standard for SPF testing. The same solar simulator using different filters can produce the Japanese Cosmetic Industry Association ("JCIA") test spectra and is used for the Persistent Pigment Darkening ("PPD") in vivo UVA protection test described below. FIG. 1 compares the COLIPA and JCIA spectra with what is generally recognized worldwide as a standard sun spectra (hereinafter "SSS") and is based on average measurements at noon on June $20^{th}$ at 40° N latitude.

In contrast to SSS, the COLIPA and JCIA spectra produced in solar simulators eliminate infrared as well as visible light. As seen in FIG. 1, a Xenon Arc solar simulator cuts off radiation at about 380 nm, meaning neither infrared nor visible radiation are emitted. Further, the filters used in solar simulator prevent wavelengths shorter than about 290 nm from being emitted. Sayre et al. have shown that SPF values as tested in the solar simulator are significantly higher than those tested in actual sunlight. For these reasons, the informational value of SPF calculated on the basis of solar simulators is questionable. It should be noted that while the SSS curve of FIG. 1 includes the light spectrum from infrared to visible to ultraviolet, it is an average spectra that varies throughout the year. Among the factors contributing to this variability are proximity and angle of the sun at different latitudes and altitudes at different times of day under variable atmospheric conditions (e.g., cloud cover).

The value of SPF as an accurate measure of protection from UVR has been further called into doubt in the scientific literature. One internationally-recognized authority in the field of photobiology aptly titled a paper "Has SPF had its day?" Several studies have shown that sunburn is as likely to occur in users of high-SPF products than users of no sunscreen at all. Indeed, some researchers have suggested that use of sunscreen products actually increases the risk of developing malignant melanoma. Thus, there exists a long-felt, but as yet unsatisfied need for a sunscreen formulation that accurately communicates photoprotection under actual conditions of use for the entire period of exposure. This need is met by present invention.

Metrics other than SPF are available for indicating degree of photoprotection provided by sunscreens. With respect to UVA protection, two of the most common test methods are the in-vitro Boots Star System and the in-vivo PPD test. The Boots Star System, based on instantaneous readings from a spectrophotometer, indicates the ratio of the average absorbance of UVA energy to UVB energy. A single star is assigned for a UVA/UVB ratio of 0.2-0.4. Two and three stars are assigned to products where the UVA/UVB ratios is 0.4-0.6 and 0.6-0.8, respectively. Four stars are assigned to products with a UVA/UVB ratio of greater than 0.8. PPD measures skin darkening two to four hours after exposure to UVR. A solar simulator emitting a spectra defined by the JCIA is used for the PPD test. However, the degree to which PPD reflects photoprotection under actual conditions of use is limited by the artificial nature of the light source.

Broad-spectrum sunscreens were developed to absorb both UVA and UVB energy. To achieve coverage over the UVA and UVB spectra, multiple sunscreens are selected both on the basis of absorbed wavelength range as well as other properties (i.e., water resistance, hypoallergenicity). A prevailing paradigm in sunscreen formulation has been "more is better". Many follow the approach that high SPF or more Boots stars can best be achieved by including many sunscreens in high concentrations. Because many sunscreens have decreased performance characteristics (e.g., lower SPF) when exposed to natural light, adherents of this school of formulation add more sunscreen actives than should theoretically be required to achieve a certain SPF. In so doing, they compensate for the degradation that takes place in the laboratory setting. However, this reasoning flawed. There is markedly more photodegradation in natural sunlight, causing the actual SPF realized by the consumer to be lower.

The "more is better" paradigm also overlooks the fact that among the degradation products in photolabile sunscreens are free radicals which can cause damage to DNA and other cellular molecules. Over time, free radical damage may become irreversible and lead to disease including cancer. Moreover, to the extent that a sunscreen is photolabile under artificial light (e.g., JCIA, COLIPA), that same composition could undergo more photodegradation, and produce more free radicals, when exposed to UVR as well as infrared and visible light under ambient conditions. Thus, a third objective of the present invention is to identify a combination sunscreen composition where after irradiation under ambient light each sunscreen active is photostable and thereby minimize the formation of potentially harmful free radicals.

Avobenzone, which absorbs both UVA I and II is among the more commonly used UVA sunscreens and has been used in combination with other sunscreens in several commercial products. For example, Bullfrog Sunscreen SPF 15 Amphibious Formula was commercially available in the 1980s and contained 2% (wt/wt) avobenzone, 10% (wt/wt) octocrylene, and a third sunscreen, ethyl dihydroxypropyl aminobenzoate. Schering Plough's Shade UVAGuard was sold in the U.S. in 1993 and contained 3% (wt/wt) avobenzone, 3% (wt/wt) oxybenzone, and a third sunscreen, 7.5% (wt/wt) octylmethoxycinnamate. Ombrelle SPF 30, sold in Canada, contained 3% avobenzone (wt/wt), 10% octocrylene (wt/wt) and two additional sunscreens, 6% oxybenzone (wt/wt) and 5% octisalate (wt/wt). Avobenzone has not, however, been combined in a sunscreen formulation as claimed in the present invention (i.e., with octocrylene, oxybenzone and no substantial amounts of additional photodegradable sunscreens, preferably substantially no additional sunscreens).

After recognizing the importance of broad spectrum coverage, sunscreen research began to focus on the effectiveness and efficiency of the protection provided. One particularly important parameter that has emerged is photostability. In published articles and meetings of national and international Societies of Cosmetic Chemists, researchers have commented that for maximum safety, broad-spectrum protection must remain efficient throughout the period of exposure to the sun. Many tests for photostability have been proposed. Of these, the majority are performed using artificial light sources (e.g., COLIPA, JCIA). For the reasons discussed above with respect to SPF and UVA protection testing, use of artificial light can strongly confound test results.

Diffey et al. "Sunscreen Product Photostability: A Key Parameter for a More Realistic In Vitro Efficacy Evaluation" *Eur. J. Dermatol.* 7: 226-228 (1997) proposes a photostability test where thin films of sunscreen product are scanned. UVA and UVB absorbance are plotted before and after irradiation, and the change in the area under the curve represents relative photostability. The Diffey protocol has several limitations. First, the sample area to be scanned by most instruments is very small, making it difficult to ascertain whether the same area was scanned before and after irradiation. If pre- and post-irradiation scans are not taken over precisely the same area, variations in film thickness will skew the results. Moreover, where a composition contains several sunscreens, it is impossible to determine the extent of change for any one sunscreen. This is important because a photolabile sunscreen may undergo significant free radical and/or chemical entity change that could go undetected by the Diffey test.

In published U.S. patent application Ser. Nos. 2004/0047818 and 2004/0047817, Bonda et al. describe a test protocol very similar to Diffey, except that photostability is judged based on absorbance at wavelength(s) of particular interest. This protocol shares the same limitations as Diffey. Further, by limiting the test spectra to artificial light at a specific wavelength, the Bonda proposed method may be even less predictive of photostability than that of Diffey.

Berset et al. "Proposed Protocol for Determination of Photostability Part 1: Cosmetic UV Filters." *Intl. J. Cosmet. Sci.*, 18(4): 167-177 (1996) teaches a photostability protocol based on comparison of UVR absorption of individual sunscreen actives in solution before and after irradiation. As discussed above, commercially-available, broad spectrum sunscreens contain multiple sunscreen actives as well as other ingredients, the interaction of which may or may not destabilize the composition. Since the Berset method does not account for these interactions, it is not sufficiently predictive of the photostability.

A more accurate approach to quantifying photodegradation, one which would account for production of free radical intermediates, is to analyze the content of individual sunscreen actives in the final commercial product before and after irradiation. Cambon et al. "An In-Vivo Method to Assess the Photostability of UV filters in a Sunscreen" *J Cosmet. Sci.*, 52: 1-11 (2001) describes a method of measuring photodegradation of sunscreen product that has been directly applied to the skin of human subjects. After irradiation with artificial light (i.e., a solar simulator), residual product is removed via tape strippings, and assayed with HPLC. The use of HPLC produces a true assessment of photodegradation of a sunscreen on exposure to the wavelengths tested. Because the light source used in the Cambon protocol is a solar simulator (i.e., as opposed to natural light), its predictiveness of photostability is limited. Moreover, the ability to control the thickness of application of sunscreen formulation to human skin in a uniform manner is inherently limited, and the absorption of different formulation components in different compositions may vary from subject to subject, with respect to both the sunscreen active and the various excipients, thereby confounding comparisons between tests made on different subjects, at different times, or with different formulations.

As discussed above, avobenzone's broad coverage in the UVA I and UVA II spectra make it a desirable sunscreen. However, avobenzone is widely recognized to be photolabile and to undergo significant photodegradation. For example, as shown in Tables 7 and 8 below, significant percentages of avobenzone were lost when a popular, commercially-available sunscreen product sold in the U.S. and labeled as having an SPF of 30 was exposed to natural sunlight. In a search for photostable broad spectrum sunscreens, researchers have attempted to combine avobenzone with other sunscreens. U.S. Pat. No. 5,576,354 (assigned to L'Oréal) claims a process for stabilizing avobenzone with respect to UV radiation of wavelengths between 280 and 380 nm by adding octocrylene, a UVB absorber, to a sunscreen having 1% to 5% (wt/wt) avobenzone, to result in a concentration of at least 1% octocrylene (wt/wt based on the sunscreen composition). U.S. Pat. No. 5,776,439 discloses a photostable composition comprising from 1% to 10% (wt/wt) avobenzone and from 0.5% to 10% oxybenzone, a UVB absorber. Published U.S. patent application Ser. No. 2004/0047818 (Bonda et al.) discloses a sunscreen composition comprising avobenzone, less than 1% octocrylene (wt/wt), and a diester or polyester of naphthalene dicarboxylic acid. The Bonda 2004/0047818 application further teaches the three sunscreens in further combination with oxybenzone. However, none of these putatively stable prior art compositions teach a sunscreen combining avobenzone, octocrylene and oxybenzone alone, with no substantial amount of other photodegradable sunscreen actives or with substantially no other sunscreen active present. U.S. Pat. Nos. 5,576,354 and 5,776,439 and published U.S. patent application Ser. Nos. 2004/0047817 and 2004/0047818 are incorporated herein by reference.

By identifying a combination sunscreen product comprising (i) a photostable triplet combination of three sunscreen actives (i.e., avobenzone, octocrylene and oxybenzone), and (ii) optionally a fourth sunscreen component selected from the group consisting of one or more sunscreens that individually are photostable and do not substantially negatively impact the photostability of the triplet sunscreens, that is (iii) substantially free of substantial amounts of other sunscreens and/or substantially free of other sunscreens (especially octisalate, octinoxate and homosalate), the present invention meets two long felt but unmet needs: (i) accurately communicating the amount of UVR photoprotection actually provided; and (ii) minimizing the amount of potential harmful free radicals formed as byproducts of photodegradation.

BRIEF DESCRIPTION OF THE INVENTION

The present invention is a novel, photostable composition that protects the skin and other substrates and products against ultraviolet light rays comprising a triplet combination of three sunscreens—avobenzone, octocrylene and oxybenzone. Compositions of the present invention provide an SPF of X and none of the three required sunscreen actives photodegrade to a concentration of less than Z, where Z is 70%, preferably 75%, and more preferably 80% of their initial concentration after exposure to Y SEDs of UVR from natural sunlight, where Y is about ½ X. Optionally, compositions of the present invention may include one or more photostable sunscreens (other sunscreens that do not degrade below a concentration Z as defined above) that do not substantially negatively impact the photostability of the triplet sunscreens. Compositions of the present invention are substantially free of substantial amounts of other photodegradable sunscreens, preferably substantially free of other photodegradable sunscreens, more preferably completely free of other photodegradable sunscreens, especially octinoxate, octisalate and homosalate. Compositions of the present invention are even more preferably substantially free of substantial amounts of all other sunscreens, still more preferable substantially free of all other sunscreens, and yet more preferably completely free of all other sunscreens.

DETAILED DESCRIPTION OF THE INVENTION

The present invention relates to a novel, photostable sunscreen composition that provides and substantially maintains a desired SPF of X throughout the period of exposure to natural sunlight and comprises a triplet combination of three sunscreen actives—avobenzone, octocrylene and oxybenzone. Each of the three required sunscreen actives photodegrades to a concentration of not less than 70%, preferably not less than 75%, and more preferably not less than 80% of their initial concentration after exposure to Y SEDs of UVR from natural sunlight, where Y is about ½ X.

Optionally, compositions of the present invention may contain a fourth sunscreen component selected from the group consisting of one or more sunscreens that are (i) individually photostable (i.e., and do not photodegrade to a concentration of less than 70%, preferably not less than 75%, more preferably not less than 80% of their initial concentration after exposure to Y SEDs of UVR from natural sunlight, where Y is about ½ X) and (ii) do not substantially negatively impact the photostability of the sunscreens in the triplet combination. For purposes of the present invention, "substantially negatively impacts" means reducing the residual percentage of any of avobenzone, oxybenzone or octocrylene to less than Q, where Q is 70%, preferably 75%, more preferably 80%, still more preferably 85%, even more preferably 90% and most preferably 95% of the initial concentration of that particular sunscreen component. In a further preferred embodiment of the present invention, "substantially negatively impacts" means reducing the residual percentage of any individual component of the triplet combination by more than 5% based the original concentration of the individual component. Residual percentage is determined by HPLC.

Compositions of the present invention are substantially free of substantial amounts of photodegradable sunscreens, preferably substantially free of photodegradable sunscreens, and more preferably substantially free of substantial amounts of all other sunscreen actives, most preferably completely free of other sunscreen actives. For purposes of the present invention, "substantially free" means less than 5%, preferably less than about 4½%, more preferably less than about 3%, and most preferably completely free of other sunscreen actives. For purposes of the present invention, a "photodegradable sunscreen" includes, but is not limited to, a sunscreen active ingredient selected from the group consisting of aminobenzoic acid, cinoxate, homosalate, menthyl anthranilate, octyl methoxycinnamate, octisalate, padimate O, and trolamine salicylate. While not photodegradable as defined above, the pigments zinc oxide and titanium dioxide are generally undesirable for inclusion in compositions of the present invention. Zinc oxide and titanium dioxide will be grouped with the photodegradable sunscreens with respect to allowable content in compositions of the invention (i.e., "substantially free of substantial amounts of . . . " or "completely free of . . . ").

Sunscreen compositions of the present invention unexpectedly have been found to maintain substantially an SPF of X throughout the period of exposure and to be photostable when irradiated with natural sunlight, irrespective of altitude, season, time of day, angle of the sun relative to the sample or atmospheric conditions (e.g., cloud cover). Each sunscreen active in the triplet combination of the present invention does not photodegrade to less than about 70%, preferably not less than about 75%, and more preferably not less than about 80% of its initial (i.e. pre-natural UV light exposure) concentration after exposure to Y SEDs of UVR from natural sunlight, where Y is about ½ X. For purposes of the present invention, "pre-natural UV sunlight exposure" is intended to mean the composition just prior to being exposed to natural sunlight in a laboratory test or in actual consumer use (i.e., in the ambient environment). Incidental UV exposure in the course of manufacture and packaging of the composition is to be neglected.

The ratio (weight/weight) of avobenzone: oxybenzone: octocrylene should preferably be in the range of a: b: c, where a is from 0.5 to 5.0, b is from 0.5 to 10, and c is from 0.5 to 10, preferably a is from 1 to 3, b is from 1 to 6, and c is from 1 to 10. Once a proper ratio is selected, the sunscreen actives can be combined in sufficient amounts to achieve a desired SPF using standard formulating techniques known to persons of ordinary skill in the art.

Avobenzone, the USAN name for butylmethoxydibenzoylmethane, is sold under various tradenames including Parsol 1789, Parsol, Eusolex 9020, Neo Heliopan 357, Photoplex, Uvinul BMBM. Other chemical names for avobenzone include: 1-(4-methoxyphenyl)-3-(4-tert-butylphenyl) propane-1,3-dione; 1-(4-tert-butylphenyl)-3-(4-methoxyphenyl) propane-1,3-dione; 4-(1,1-dimethylethyl)-4'-methoxydibenzoylmethane; 4-methoxy-4'-tert-butyldibenzoylmethane; and 4-tert-butyl-4'-methoxydibenzoylmethane.

Oxybenzone, also known as benzophenone-3, is sold under various tradenames including Aduvex 24, Advastab 45, Anuvex, ASL 24, Chimassorb 90, Cyasorb UV 9 Light Absorber, Cyasorb UV 9, Escalol 567, Neo Heliopan BB, NSC 7778, Ongrostab HMB, Onzone, Seesorb 101, SpectraSorb UV 9, Sumisorb 110, Syntase 62, Tinosorb B 3, Uvasorb Met/C, Uvinul M 40, Uvinul 3040, Uvinul 9, Uvistat 24, and Viosorb 110. Other chemical names for oxybenzone include: (2-hydroxy-4-methoxyphenyl) phenylmethanone; 2-benzoyl-5-methoxyphenol; 2-hydroxy-4-methoxybenzophenone; and 4-methoxy-2-hydroxybenzophenone.

Octocrylene is sold under various tradenames including Agent AT 539, "Eusolex OCR, Neo Heliopan 303, Sanduvor 3039, Uvinul N 539, Uvinul N 539SG, Uvinul N 539T, Uvinul 3039, Viosorb 930. Other chemical names for octocrylene include: 2-cyano-3,3-diphenylacrylic acid 2-ethylhexyl ester 2-ethylhexyl α-cyano-β-phenylcinnamate; 2-ethylhexyl α-cyano-β, β'-diphenylacrylate; 2-ethylhexyl 2-cyano-3,3-diphenyl-2-propenoate; 2-ethylhexyl 2-cyano-3,3-diphenylacrylate; 2'-ethylhexyl 2-cyano-3-phenylcinnamate.

As described above, a sunscreen composition of SPF X is considered to be "photostable" when at least 70%, preferably at least 75%, more preferably at least 80% of each sunscreen active in the composition remains after exposure of the composition to Y SEDS of natural sunlight, where Y is about ½ X. "Photostability" is assessed by (i) assaying the pre-UVR exposure concentration of each sunscreen active present in the sunscreen composition by high-performance liquid chromatography ("HPLC"); (ii) applying a sample of the sunscreen composition at a concentration of 2 mg/cm$^2$ (a standard concentration used in SPF testing) to a non-coated microscope slide or similar non-reactive surface (e.g., glass or quartz plate); (iii) irradiating the sample in natural sunlight according to a dosing regimen as illustrated in Table 1; (iv) assaying the concentration of each sunscreen active post-UVR exposure.

TABLE 1

Dosing Regimen

| | SEDs Irradiated | | | | |
|---|---|---|---|---|---|
| SPF | 1 | 2 | 4 | 8 | 16 |
| 2 | x | | | | |
| 4 | x | x | | | |
| 8 | x | x | x | | |
| 16 | x | x | x | x | |
| ≧30 | x | x | x | x | x |

More specifically, after the desired UVR exposure, each slide is removed from sunlight and placed in a sealed Blue Max™ polypropylene conical tube (Becton Dickinson) or similar container, and stored in an area to prevent further exposure to natural sunlight. When an irradiation series is completed, the residual content of each sunscreen active is determined via HPLC, such as the Perkin Elmer Model 200, equipped with a 785 UVN detector, and a C18 column. A detector wavelength of 310 nm and an eluent solution of 85/15 phosphoric acid solution may be used. The sunscreen composition is extracted from the slide with isopropanol or other suitable solvent and sonicated for a minimum of 10 minutes to completely solubilize the sunscreen actives. The solution is then filtered with a 0.45 um GHP13 mm syringe filter. The above analytical procedure may be modified in a manner that would be obvious to the person of ordinary skill in the art.

Based on the above analytical method, surprisingly it has been discovered that many sunscreen actives reported to be photostable based on laboratory tests using artificial sunlight sources (e.g., COLIPA, JCIA spectra) are in fact photodegradable when exposed to natural sunlight.

Because the sunscreen compositions of the present invention are photostable, lesser amounts of sunscreen actives are needed to obtain an SPF. For purposes of the present invention "sunscreen efficiency" is expressed by the ratio SPF/total sunscreen active % (wt/wt). The sunscreen compositions of the present invention have a sunscreen efficiency greater than 2, preferably at least about 3, and more preferably at least about 4. Table 2 compares the sunscreen efficiencies of commercial products with those of the invention. The SPF 70 product of the invention had a sunscreen efficiency more than 2½ times greater than a comparable commercial SPF 70 product.

TABLE 2

Comparative Sunscreen Efficiency

| Sunscreen Composition | % Sunscreen | Sunscreen Efficiency |
|---|---|---|
| Commercial SPF 30 | 17.5 | 1.71 |
| Commercial SPF 40 | 26.5 | 1.51 |
| Commercial SPF 50 | 33.5 | 1.49 |
| Commercial SPF 70 | 35.5 | 2.00 |
| Invention SPF 30 | 7.5 | 4.00 |
| Invention SPF 60 | 13 | 4.61 |
| Invention SPF 70 | 13 | 5.38 |

Apart from formulating efficiencies, the photostability of compositions of the present invention imparts another benefit—minimizing the formation of potentially harmful free radicals (i.e., in photodecay products). First, since individual sunscreen actives are used in smaller quantities, lesser amounts of photoreactive sunscreens are available to form free radicals. Relatedly, as a consequence of their photostability, compositions of the present invention can be applied less frequently, again minimizing potential free radical formation.

Photoprotective compositions of the present invention may be prepared according to principles and techniques generally known to those skilled in the cosmetic and pharmaceutical arts. Octocrylene and oxybenzone are added under heat to a cosmetically acceptable vehicle and mixed until homogeneous. Avobenzone is then added to this mixture. Cosmetically acceptable vehicles useful for preparing compositions of the present invention are well-known to persons of ordinary skill in the art and include lotions, creams, sprays, gels, wax-type sticks, oils, milks and mousses. Such vehicles can be emulsions of the water-in-oil, oil-in-water or water-in-silicone types. The vehicle contains one or more diluents well-known to persons of ordinary skill in the art including, but not limited to, rheology modifiers, emulsifiers, pH modifiers, moisturizers (e.g., aloe extract), humectants, emollients (e.g., caprylic/capric triglycerides), structuring agents (e.g., beeswax, candelilla wax, paraffin), stabilizers, lubricants, fragrances, preservatives (e.g., propylparaben), colored pigments or coloring agents. Typical, non-limiting composition vehicles and excipients can also be found in the following U.S. patents, each of which is incorporated in its entirety by reference with respect to such vehicles and excipients: 4,015,009; 4,024,106; 4,455,295; 4,613,499; 4,710,373; 4,863,963; 5,160,731; 5,338,539; 5,426,210; 5,783,173; and 5,917,088.

The following examples are further illustrative of the present invention. The components and specific ingredients are presented as being typical, and various modifications can be derived in view of the foregoing disclosure within the scope of the invention.

EXAMPLE 1

Sunscreen Comparison

Formulation 1, a photostable sunscreen composition with an SPF of 50, was prepared according to the procedure set forth below.

| | Formula 1* (Invention) | Formula 2 (Comparison) | Formula 3 (Comparison) |
|---|---|---|---|
| Phase A | | | |
| Ozokerite | 9 | 9 | 9 |
| Beeswax | 6 | 6 | 6 |
| Candelilla Wax | 4 | 4 | 4 |
| Paraffin | 9 | 9 | 9 |
| Octocrylene | 10 | 1.6 | 10 |
| Oxybenzone | 6 | 6 | 6 |
| Aloe Extract | 0.0823 | 0.1 | 0.1 |
| Homosalate | — | 15 | 15 |
| Octisalate | — | 5 | 5 |
| Octinoxate | — | 7.5 | 7.5 |
| Caprylic/Capric Triglycerides | 9 | 9 | 6.8 |
| Diisobutyl Adipate | 15 | 6 | 5 |
| Silica | 2 | 2 | 1.5 |
| Flora/Nut Extracts | 0.1 | 0.1 | 0.1 |
| Vitamins A, C & E | 0.01 | 0.01 | 0.01 |
| Propylparaben | 0.1 | 0.1 | 0.1 |
| BHT | 0.01 | 0.01 | 0.01 |
| Hexacaprylate/Hexacaprate | 14.58 | 4 | 2.88 |
| Vitamin E | 0.00154 | — | — |
| Mineral Oil | 0.00123 | — | — |
| Avobenzone | 3 | 2 | 2 |
| Phase B | | | |
| Fragrance | 0.11462 | — | — |
| Cyclomethicone | 12 | 13.58 | 10 |

*Unless otherwise stated, percentages are weight/weight.

With the exception of the avobenzone, combine the ingredients of Phase A and mix until uniform. Add avobenzone. Continue mixing at about 75° C. until a uniform fluid mixture is obtained. Cool while stirring. At about 50° C. add the Phase B ingredients. Continue mixing and cool to about 40° C.

To compare the photostability of Formulas 1 and 2, a uniform 2 mg/cm$^2$ film of sunscreen product was placed on multiple microscope slides. The slides were exposed to direct sunlight for time intervals corresponding to 1, 2, 4, 8, and 16 SEDs as measured by a Solar Light PMA 2100 detector. (Unless otherwise indicated, all sunlight exposures were in Ormond Beach, Fla.). Slides were removed from the sun after the desired exposure and stored in Blue Max™ polypropylene conical tubes. Upon completion of the test series, samples were dissolved in a suitable solvent, sonicated and then assayed via HPLC. Residual avobenzone content is reported as a percentage of sunscreen remaining after UVR exposure is presented in Table 3. Unless otherwise indicated, all assays were performed by HPLC with oxybenzone, if present, as the internal standard.

TABLE 3

Residual Avobenzone

| SEDs | Formula 1 | Formula 2 (Trial 1) | Formula 2 (Trial 2) | Formula 3 |
|---|---|---|---|---|
| 1 | 100% | 73% | 95% | 69% |
| 2 | 100% | 42% | 90% | 57% |
| 4 | 99% | 33% | 79% | 35% |
| 8 | 96% | 19% | 64% | 25% |
| 16 | 94% | — | 42% | — |

Residual concentration of avobenzone, octinoxate, and octisalate in Formula 2 was further investigated by exposing samples to natural sunlight at various hours in the day and times of the year, as well as to artificial spectra. The results are presented in Tables 4, 5 and 6.

TABLE 4

Formula 2 (Residual % of Avobenzone)

| SEDs | COLIPA | JCIA | 2/25 | 3/31 | 4/17 | 5/5 | 5/20 | 5/28* | 5/18[a] | 7/6[a] |
|---|---|---|---|---|---|---|---|---|---|---|
|  | — | 89% | 73% | 67% | 73% | 92% | 95% | 75% | 80% | 89% |
| 2 | 99% | 80% | 48% | 48% | 42% | 85% | 90% | 70% | 73% | 78% |
| 4 | 96% | 58% | — | 35% | 33% | 78% | 79% | 60% | 60% | 65% |
| 8 | 89% | 58% | — | 25% | 19% | 62% | 64% | 29% | 44% | 55% |
| 16 | 77% | — | — | — | — | 45% | 42% | 19% | 26% | 21% |

TABLE 5

Formula 2 (Residual % of OMC)

| SEDs | COLIPA | JCIA | 2/25 | 3/31 | 4/17 | 5/5 | 5/20 | 5/28* | 5/18[a] | 7/6[a] |
|---|---|---|---|---|---|---|---|---|---|---|
| 1 | — | 78% | 60% | 57% | 61% | 66% | 69% | 61% | 63% | 66% |
| 2 | 78% | 72% | 51% | 51% | 46% | 61% | 63% | 58% | 60% | 59% |
| 4 | 69% | 59% | — | 42% | 43% | 59% | 58% | 53% | 54% | 54% |
| 8 | 64% | 61% | — | — | 28% | 52% | 52% | 42% | 49% | 49% |
| 16 | 58% | — | — | — | — | 46% | 45% | 37% | 41% | 35% |

TABLE 6

Formula 2 (Residual % of Octisalate)

| SEDs | COLIPA | JCIA | 2/25 | 3/31 | 4/17 | 5/5 | 5/20 | 5/28* | 5/18[a] | 7/6[a] |
|---|---|---|---|---|---|---|---|---|---|---|
| 1 | 99% | 98% | 99% | 96% | 97% | 96% | 84% | — | 98% | 97% |
| 2 | 100% | 97% | 95% | 97% | 91% | 95% | 94% | 77% | 98% | 96% |
| 4 | 99% | 97% | — | 96% | 87% | 88% | 89% | 74% | 96% | 94% |
| 8 | 99% | 97% | — | — | 83% | 79% | 81% | 59% | 93% | 91% |
| 16 | 98% | — | — | — | — | 64% | 68% | 52% | 90% | 76% |

*Irradiated over 3 days in early morning sun.
[a]Tests conducted in 2004. Other tests were conducted in 2003.

The photodegradation of avobenzone (as expressed as a residual percentage) was further studied by comparing Formula 1 with a popular, commercially-available sunscreen product sold in the US and labeled as having an SPF of 30. This "Commercial 30" product is an oil-in-water emulsion with sunscreen actives listed on the label and assayed to be approximately 3% oxybenzone, 2% avobenzone, 7.5% OMC, 5% octisalate, and 7% homosalate. The Commercial 30 product as tested on two dates (Trials 1 and 2) is presented in Table 7 below.

TABLE 7

Percent Residual Avobenzone

|  | Commercial 30 | | |
|---|---|---|---|
| SEDs | (Trial 1) | (Trial 2) | Formula 1 |
| 1 | 25% | 74% | 100% |
| 2 | 7% | 60% | 100% |
| 4 | 3% | 41% | 99% |
| 8 | 0% | 19% | 96% |
| 16 | — | 6% | 94% |

Exposure Date for Trial 1: Apr. 07, 2003
Exposure Date for Trial 2: May 07, 2003
Exposure Date for Formula 1: May 07, 2003

EXAMPLE 2

Sunscreen Comparison

The trio of sunscreens of the present invention—octocrylene, oxybenzone and avobenzone—were combined in a prior art sunscreen formulation in the following weight/weight ratios: 10% octocrylene, 6% oxybenzone, 3% avobenzone and 5% octisalate. Two formulations, the trio sunscreens of the present invention (Formula 4) and the prior art quartet of sunscreens (Formula 5), were prepared according to the procedure set forth below.

| Ingredients | Formula 4 (Invention) | Formula 5 (Prior art) |
|---|---|---|
| Phase A | | |
| Microcrystalline Wax | 0.5 | 0.5 |
| Polyethylene, Stearoxy Dimethicone | 0.5 | 0.5 |
| Beeswax | 0.5 | 0.5 |
| Oxybenzone | 6.0 | 6.0 |
| Octocrylene | 10.0 | 10.0 |
| Octisalate | — | 5.0 |
| Disopropyl Adipate | 5.0 | 5.0 |

-continued

| Ingredients | Formula 4 (Invention) | Formula 5 (Prior art) |
|---|---|---|
| Dimethyl Capramide | 2.0 | 2.0 |
| Cetyl Dimethicone Copolyl | 3.0 | 3.0 |
| Ethylhexyl Palmitate | 5.0 | 5.0 |
| Methylparaben | 0.3 | 0.3 |
| Propylparaben | 0.1 | 0.1 |
| Phase A-1 | | |
| Avobenzone | 3.0 | 3.0 |
| Hydrated Silica | 3.0 | 3.0 |
| Phase B | | |
| Water | QS | QS |
| Flora/Nut Extracts | 0.1 | 0.1 |
| Sodium Chloride | 0.7 | 0.7 |
| Disodium EDTA | 0.05 | 0.05 |
| Aloe Concentrate | 0.1 | 0.1 |
| Phase B-1 | | |
| Acrylates Copolymer | 1.0 | 1.0 |
| Phase C | | |
| Benzyl alcohol | 1.0 | 1.0 |
| Glycacil L | 0.3 | 0.3 |
| Fragrance | 0.6 | 0.6 |
| Vitamin A, C, E Complex | 0.01 | 0.01 |

Mix and heat Phase A at approximately 75° C. until uniform. Add Phase A-1 and mix. Separately heat and mix Phase B at 75° C. Add and mix Phase B-1 to Phase B. Add Phases B and B-1 to Phases A and A-1. Cool while mixing to approximately 50° C. and add and mix Phase C. Cool to about 35° C. while mixing.

Formulas 4 and 5 are compared in Table 8 with respect to SPF and UVA/UVB ratio. More specifically, an in vitro analysis comparing the two formulas was performed by applying a 2 mg/cc of product to Vitro-Skin® (IMS Inc., Milford, Conn.). After UVR exposure, the plates were analyzed by an Optimetrics SPF 290.

TABLE 8

SPF and UVA/UVB

| Test | Formula 4 | Formula 5 |
|---|---|---|
| SPF | 136 | 153 |
| UVA/UVB Ratio | .745 | .745 |

There is no significant difference between SPF 136 and SPF 153 which, represent, respectively, 99.26% and 99.35%, absorbance of erythemal energy. The two SPFs are within experimental error and considered identical. Thus, there is no benefit in terms of increased photoprotection by adding octisalate. However, as illustrated in Table 9, when exposed to natural sunlight as in Example 1, octisalate is photolabile. Octisalate undergoes significant photodegradation, thereby creating an increased risk of free radical formation.

TABLE 9

Residual Octisalate

| SEDs | Residual % |
|---|---|
| 1 | 96% |
| 2 | 100% |
| 4 | 92% |
| 8 | 80% |
| 16 | 55% |

U.S. patent applications Ser. Nos. 2004/0047817 and 2004/0047818 teach that avobenzone derivatives can be stabilized by one or more diesters and polyesters of naphthalene dicarboxylic acids ("DNDA") in the presence of low and very low levels of octocrylene. DNDA is supplied commercially by Hall Star under the trade name of Corapan TQ. Surprisingly, the inventor discovered that when sunscreen compositions containing DNDA as well as octocrylene and oxybenzone in meaningful amounts are irradiated with natural sunlight (i.e., actual conditions of use), the DNDA did not increase the photostability of avobenzone. Table 10 shows residual avobenzone after irradiation with 16 SEDs of natural sunlight in formulas with and without DNDA. Ingredients in each sample formula are listed on a weight/weight %. Accordingly, sunscreen compositions of the present invention are substantially free of DNDA.

TABLE 10

Triplet Combination, Corapan TQ and Octisalate

| | #1 | #2 | #3 | #4 | #5 | #6 |
|---|---|---|---|---|---|---|
| Avobenzone | 3 | 3 | 3 | 3 | 3 | 3 |
| Oxybenzone | 6 | 6 | 6 | 6 | 6 | 6 |
| Octocrylene | 10 | 10 | 10 | 10 | 10 | 10 |
| Octisalate | 5 | 5 | — | — | 5 | 5 |
| Corapan TQ | — | 5 | — | 5 | — | 5 |
| Avobenzone (% Residual) | 88% | 88% | 91% | 91% | 84% | 85% |

Dates of Exposures (Samples 1–4): Jun. 24, 2004
Dates of Exposures (Samples 5–6): Jul. 06, 2004

U.S. Pat. No. 5,776,439 teaches photostabilization of avobenzone by oxybenzone. This teaching is based on (i) use of a solar simulator as the source of UVR and (ii) absorbance at the maximum wavelength as measured two and four hours after irradiation. For the reasons discussed above, photostability testing under artificial light is not indicative of photostability under the full spectra of radiation from natural sunlight. Surprisingly, as illustrated in Table 11, the present inventor has discovered that the combination of oxybenzone and octocrylene stabilizes avobenzone more than oxybenzone or octocrylene alone. Even more surprisingly, the inventor has discovered that compositions comprising avobenzone, octocrylene and oxybenzone are photostable up to 16 SEDs in natural sunlight.

TABLE 11

Residual % Avobenzone

| | Sample 1 | Sample 2 | Sample 3 | Sample 4 |
|---|---|---|---|---|
| Avobenzone | 3 | 3 | 3 | 3 |
| Oxybenzone | — | 6 | — | 6 |
| Octocrylene | — | — | 10 | 10 |
| Avobenzone (Residual %) | 18% | 72% | 89% | 98% |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A composition that provides protection from ultraviolet radiation from natural sunlight and is photostable in natural sunlight consisting essentially of
   (a) a triplet combination of sunscreens consisting of avobenzone, octocrylene and oxybenzone;
   (b) optionally, a fourth sunscreen component selected from the group consisting of one or more sunscreens that
      (i) individually are photostable; and
      (ii) do not substantially negatively impact the photostability of the individual sunscreens in the triplet combination and
   (c) containing no diesters or polyesters of naphthalene dicarboxylic acid.

2. The composition of claim 1 consisting essentially of said triplet combination of sunscreens and substantially free of substantial amounts of any other sunscreen.

3. The composition of claim 1 having as the only sunscreens avobenzone, octocrylene and oxybenzone.

4. The composition of claim 1 wherein avobenzone, oxybenzone, and octocrylene are present in the ratio a:b:c, where a is from 0.5 to 5, b is from 0.5 to 10, and c is from 0.5 to 10.

5. The composition of claim 1 wherein avobenzone, oxybenzone, octocrylene are present in the ratio a:b:c, where a is from 1 to 3, b is from 1 to 6, and c is from 1 to 10.

6. The composition of claim 1 further comprising one or more diluents selected from the group of rheology modifiers, emulsifiers, pH modifiers, moisturizers, humectants, emollients, stabilizers, lubricants, fragrances, preservatives, colored pigments and coloring agents.

7. The composition of claim 1 wherein the composition form is a lotion, cream, spray, gel, wax-type stick, oil, milk or mousse.

8. A method of protecting the skin from damage caused by ultraviolet radiation from natural sunlight comprising applying the formulation of claim 1 to the skin.

9. A method of making the formulation of claim 1 by adding avobenzone to a composition containing octocrylene and oxybenzone.

10. A method of minimizing free radical formation in a sunscreen composition on exposure to ultraviolet radiation from natural sunlight comprising incorporating into said composition a triplet combination of organic ultraviolet radiation absorbing compounds that is photostable when exposed to ultraviolet radiation consisting essentially of octocrylene, oxybenzone and avobenzone.

11. The method of claim 10 wherein said sunscreen composition further comprises
   (a) a fourth sunscreen component selected from the group consisting of one or more sunscreens that
      (i) individually are photostable; and
      (ii) do not substantially negatively impact the photostability of the individual sunscreens in the triplet combination; and
   (b) contains no diesters or polyesters of naphthalene dicarboxylic acid.

12. A method of maximizing SPF by preparing the composition of claim 1.

13. A method of maintaining desired SPF during a period of exposure to natural sunlight by applying the composition of claim 1 to a surface in need thereof.

14. A method of reducing sunscreen usage in a consumer in need thereof comprising applying the composition of claim 1 to the skin.

15. A composition for providing a photostable SPF to a cosmetic product, hair care product or personal care product comprising adding a composition of claim 1 to such a product.

16. A method of imparting photostable protection from ultraviolet radiation from natural sunlight to a substrate comprising adding a composition of claim 1 to said substrate.

17. A method of imparting photostable protection from ultraviolet radiation from natural sunlight to a product comprising incorporating avobenzone, octocrylene and oxybenzone into said product.

18. The method of claim 16, substantially free of substantial amounts of photodegradable sunscreens.

19. A sunscreen composition that is photostable in natural sunlight and having substantially the same SPF when exposed to the same amount of ultraviolet radiation from natural sunlight as when exposed to an artificial source of ultraviolet radiation that emits the COLIPA spectra.

20. A method for providing a photostable SPF during exposure to ultraviolet radiation from natural sunlight to a cosmetic product, hair care product or personal care product comprising adding a composition of claim 1 to such a product.

21. The composition of claim 1 having an SPF efficiency greater than two.

22. The composition of claim 1 having an SPF efficiency of at least about three.

23. The composition of claim 1 having an SPF efficiency of at least about four.

24. The composition of claim 1 having substantially the same SPF throughout the period of exposure to ultraviolet radiation from natural sunlight.

25. The composition of claim 1 having an SPF of at least about 2.

26. The composition of claim 1 having an SPF of at least about 15.

27. The composition of claim 1 having an SPF of at least about 30.

28. The composition of claim 1 having an SPF of at least about 40.

29. The composition of claim 1 having an SPF of at least about 50.

30. The composition of claim 1 having an SPF of at least about 60.

31. The composition of claim 1 having an SPF of at least about 70.

32. A composition that provides protection from ultraviolet radiation from natural sun light and is photostable in natural sun light consisting essentially of
   (a) a triplet combination of sunscreens consisting of avobenzone, octocrylene and oxybenzone;

(b) optionally, a fourth sunscreen component selected from the group consisting of one or more sunscreens that
  (i) individually are photostable; and
  (ii) do not substantially negatively impact the photostability of the individual sunscreens in the triplet combination;

(c) free of aminobenzoic acid, cinoxate, homosalate, menthyl anthranilate, octyl methoxycinnamate, octisalate, padimate 0, trolamine salicylate, zinc oxide and titanium dioxide; and (d) free of diesters or polyesters of naphthalene dicarboxylic acid.

* * * * *